US009218055B2

(12) United States Patent
Sakaguchi et al.

(10) Patent No.: US 9,218,055 B2
(45) Date of Patent: Dec. 22, 2015

(54) DEVICES, SYSTEMS, AND METHODS FOR EMPATHETIC COMPUTING (71) Applicant: SomniQ, Inc., Menlo Park, CA (US)

(72) Inventors: Rikko Sakaguchi, Menlo Park, CA (US); Hidenori Ishikawa, Los Altos, CA (US)

(73) Assignee: SomniQ, Inc., Menlo Park, CA (US)

( * ) Notice: Subject to any disclaimer, the term of this patent is extended or adjusted under 35 U.S.C. 154(b) by 209 days.

(21) Appl. No.: 14/085,174

(22) Filed: Nov. 20, 2013

(65) Prior Publication Data
US 2014/0139466 A1 May 22, 2014

Related U.S. Application Data (60) Provisional application No. 61/728,963, filed on Nov. 21, 2012.

(51) Int. Cl.
*G06F 3/01* (2006.01)
*G06F 1/16* (2006.01)
*A61B 5/16* (2006.01)

(52) U.S. Cl.
CPC ............... *G06F 3/011* (2013.01); *A61B 5/165* (2013.01); *G06F 1/1613* (2013.01); *G06F 1/1694* (2013.01); *G06F 3/014* (2013.01); *G06F 3/015* (2013.01); *G06F 2203/011* (2013.01)

(58) Field of Classification Search
CPC ......... G06F 3/011; G06F 3/014; G06F 3/015; G06F 1/1613; G06F 1/1694; G06F 2203/011; A61B 5/165
USPC ................................. 345/156–184
See application file for complete search history.

(56) References Cited

U.S. PATENT DOCUMENTS

| D601,564 S | * | 10/2009 | Maeno | D14/400 |
| D732,033 S | * | 6/2015 | Sakaguchi | D14/388 |
| 2004/0250218 A1 | | 12/2004 | Wecker et al. | |
| 2007/0135689 A1 | | 6/2007 | Asukai et al. | |
| 2010/0144436 A1 | * | 6/2010 | Marks et al. | 463/36 |

FOREIGN PATENT DOCUMENTS

| JP | 2001-025984 A | 1/2001 |
| KR | 2009-0093286 | 9/2009 |
| KR | 2012-0092316 | 6/2012 |

OTHER PUBLICATIONS

Yang Cai, Empathic Computing, 2006, Ambient Intelligence in Everyday Life, LNAI 3864, pp. 67-85.*
International Search Report and Written Opinion for International Application No. PCT/US2013/070976, mailed Mar. 24, 2014.

* cited by examiner

Primary Examiner — Dmitriy Bolotin
(74) Attorney, Agent, or Firm — Dorsey & Whitney LLP (57) ABSTRACT Devices, systems, and methods for empathetic computing are described herein. An example empathetic computing device includes an enclosure configured to fit into the palm of a user. The enclosure may have an upper portion and a lower portion and comprise an interface board, a processor, and a touch sensor. The interface board may have a plurality of light emitting devices configured to provide a light pattern of a visual response. The processor may be coupled to a memory device. The touch sensor may be configured to detect the touch of the user. The touch sensor may comprise a touch belt disposed along the enclosure circumferentially and a touch pad.

23 Claims, 8 Drawing Sheets

DEVICES, SYSTEMS, AND METHODS FOR EMPATHETIC COMPUTING

This application claims priority to U.S. Provisional Application No. 61/728,963 filed Nov. 21, 2012, which application is incorporated herein by reference, in its entirety, for any purpose.

TECHNICAL FIELD

Examples described herein relate generally to empathetic computing systems, including computing systems having a humanized interface for interfacing with a user.

BACKGROUND

Computing systems have become ubiquitous in our daily lives. A user interacts with a computing system (e.g., a computer) through a user interface, which is typically a graphical user interface. Graphical user interfaces of currently known computing systems typically necessitate use of certain hardware, such as keyboards, pointer devices (e.g., mice, trackpads, and the like), monitors, and more recently touch screen interfaces, in order to enable the user to interact with the machine (e.g., computer). For example, a user may be required to push a button on a keyboard or a pointer device or tactually input specific information via a touch screen interface in order to effect a communication or interaction with the computer. Correspondingly, information is communicated back to the user typically graphically on a computer monitor (e.g., an LCD screen or similar display devices). Use of conventional user interfaces accordingly requires explicit commands to be provided by entering specific information on an input device. Computing systems generally are unable to interact seamlessly with users by, for example, reacting to natural movements of users.

DETAILED DESCRIPTION

As discussed above, while use of such interaction may be relatively conventional, fundamentally new and different techniques and systems for interfacing with a computer may be desired. Such techniques and systems may be particularly appreciated in applications directed to memorializing aspects of a person's life where conventional interaction may prove too cumbersome, distracting, and/or impersonal to be effective or desirable.

For example, it is widely known that trying to bring attention to one's own state of mind is an early step in raising self-awareness. A simple act of noticing, appreciating and/or learning from everyday activities may produce a positive effect that deepens a person's consciousness about his or her own behavior. Briefly, self-awareness may allow a user to focus on broader desires and goals. Maintaining a heightened self-awareness through constant effort in daily life nurtures mindfulness, which in turn provides more opportunities to realize something new and further improve self-awareness.

However, a habit of mindfulness is not developed instantaneously, requiring both constant and continuous effort to reflect and review oneself. To facilitate such reflections on a daily basis, there are many proven approaches such as keeping a diary, performing self-reflection rituals, and implementing guided self-help practices.

While opportunities to achieve mindfulness abound in the minutiae of daily life, most are overlooked, unnoticed, and/or forgotten. It is simply impossible to make note of, or even be conscious of, every moment. Many efforts using personal computers, smartphones, and other computing devices have strived to capture these opportunities in daily life, thereby allowing a person track his/her activities, categorize his/her moods or emotions, or record moments for later review.

However, none of these efforts effectively overcome issues pertaining to the short attention spans of users. Often opportunities to achieve deeper realization are ignored or forgotten because interfacing with a device during device operation, including touching a screen on a smartphone, typing text on a keyboard, using a mouse, or navigating an interface, requires a users attention and inevitably distracts the user. In particular, the opportunity to bring the user's attention to his/her own inner state of mind may only last for a brief moment, and is easily missed or ignored, even from relatively small distractions.

An additional problem with conventional methods has been maintaining user effort over time. The need for repetitive operation of a device to capture opportunities can diminish a user's motivation to pursue mindfulness as usage of the device for this purpose may feel increasingly cumbersome over time. Efforts to capture opportunities often do not last long and pursuing mindfulness becomes difficult to achieve without a better approach.

Accordingly, embodiments of the present invention may enable the user to capture opportunities in daily life that may lead to improved self-awareness and mindfulness, while mitigating the effort required of a user to capture such events. In contrast to conventional approaches, a user may easily and consistently be aware of his or her state of mind by interlacing with a device through simple and easy interactions, such as those based on natural human behavior.

Devices, systems, and methods for empathetic computing are described herein. Certain details of described examples as provided in the following description and drawings are set forth below to provide a sufficient understanding of embodiments of the invention. However, it will be clear to one skilled in the art that embodiments of the invention may be practiced without these particular details. For example, aspects of the present disclosure, as generally described herein and illustrated in the drawings, can be arranged, substituted, combined, separated, and designed in a wide variety of different configurations, all of which are implicitly contemplated herein. In some instances, well-known circuits, control signals, timing protocols, and software operations have not been shown in detail in order to avoid unnecessarily obscuring the invention.

Figure 1:
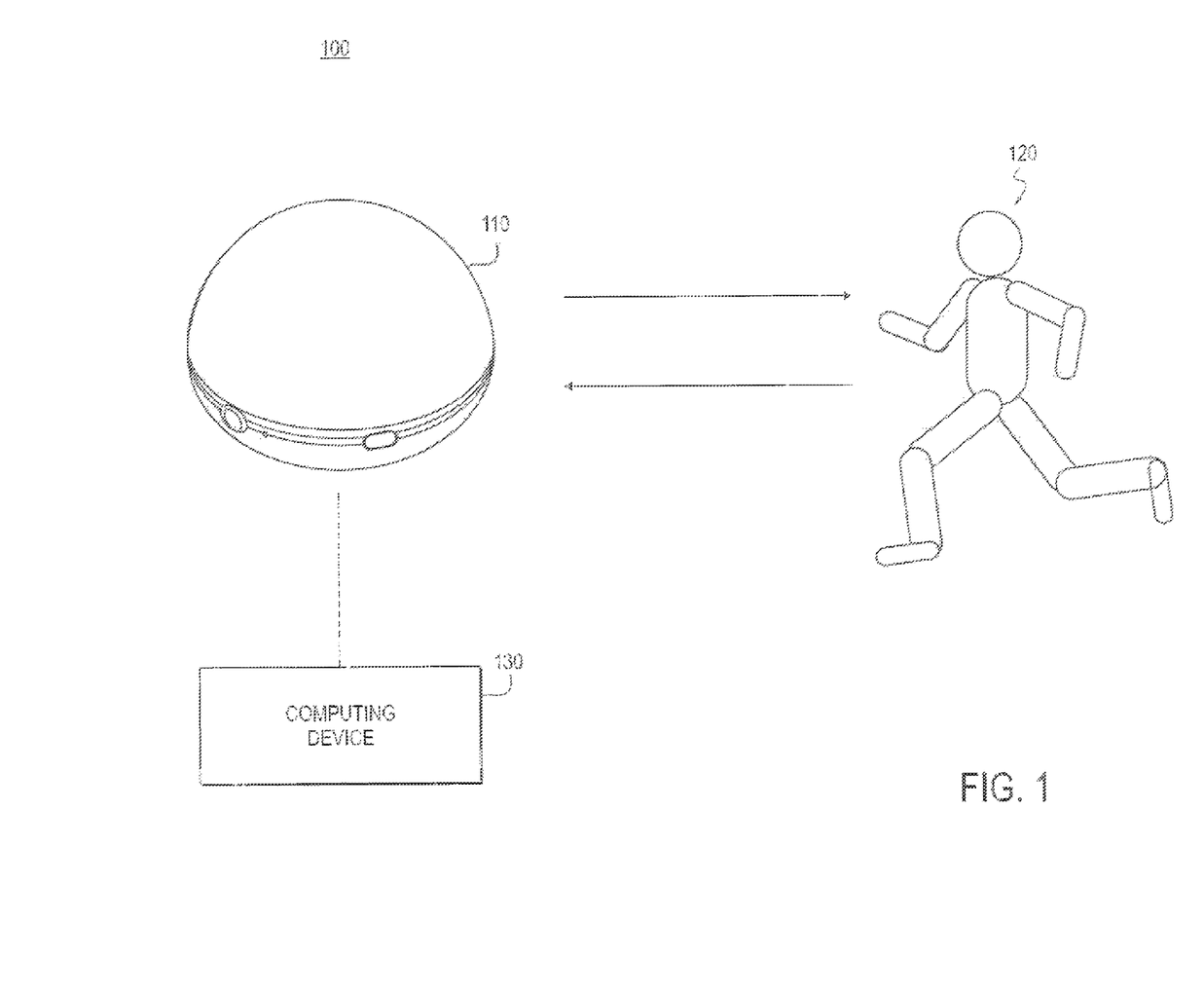
FIG. 1 is a schematic diagram of an empathetic computing system according to an embodiment of the present invention.

FIG. 1 is a block diagram of an empathetic computing system 100 according to an embodiment of the present invention. The empathetic computing system 100 includes an empathetic computing device 110, a user 120, and a computing device 130.

The empathetic computing device 110 may interlace with the user 120 using an empathetic interface. For example, the empathetic computing device 110 may interface with the user 120 without the use of conventional tactile input devices (e.g., keyboard, mouse), or using fewer conventional tactile input devices than is common. Generally, the empathetic interface may rely not on explicit commands given, by a user, but rather on natural actions of the user 120 and user interaction with the empathetic computing device 110 by the user 120.

In operation, the empathetic computing device 110 may identify one or more events associated with the user 120 and based on the identified event(s), may selectively provide a response to the user 120 and/or enter a particular mode of operation. In some examples, the empathetic computing device 110 may further capture (e.g., store) identified events. While only a single user 120 is illustrated in FIG. 1, in some examples, the empathetic computing system 100 may include a plurality of users 120 and the empathetic computing device may identify events associated with one or more of the plurality of users 120 and selectively provide a response to each of the plurality of users 120 based on the identified events.

The empathetic computing device 110 may generate data using one or more sensors included in the empathetic computing device 110. Data may be generated using sensors including, but not limited to, proximity sensors (e.g. passive infrared sensors), accelerometers, compasses, gyroscopes, light sensors, touch sensors, heat sensors, pressure sensors, and barometers, and further may be generated using various devices, such as communication devices (e.g., wireless Ethernet devices, Bluetooth devices), cameras, and microphones. The empathetic computing device 110 may further filter data using one or more filters to modify data prior to indentifying events based on the data. Generally, the empathetic computing device 110 may observe the user 120 to generate personal data and further may observe the environment of the user 120 to generate environmental data. Such data may be cumulatively referred to herein as user data and may be used to indentify events and/or selectively provide responses.

In some examples, the empathetic computing device 110 may include one or more non-volatile memory devices (e.g., flash memory, PCM memory) for storing user data. Optionally, the non-volatile memory device may be a removable non-volatile memory device, such as a micro SD memory card. Additionally, or alternatively, the empathetic computing device 110 may store data on the computing device 130. The empathetic computing device 110 may provide data to the computing device 130 over a network (e.g., LAN, WLAN) or using other data transfer methodologies. Data may be stored in real-time or may be stored periodically.

Based on the user data, the empathetic computing device 110 may identify events. Identifying an event may include identifying natural actions of the user 120. As further described herein, natural actions of the user 120 may include, but are not limited to, laughing, talking, winking, making a facial expression (e.g., smiling, frowning), or a combination thereof. Identifying an event may further include identifying user interaction with the empathetic computing device 110 by the user 120. In some instances, for example, the empathetic computing device 110 may both determine the proximity of the user 120 and differentiate whether the empathetic computing device 110 is being touched, supported (e.g., on a flat or curved palm), partially grasped, fully grasped, clasped, or a combination thereof, by a user 120. The empathetic computing device 110 may further identify environmental factors of the user 120, such as location, weather, temperature, time, ambient brightness, and ambient noise.

After one or more events have been identified, the empathetic computing device 110 may provide responses to the user 120 and/or may enter a particular mode of operation. Generally, the empathetic computing device 110 may provide a visual, auditory, and/or vibrational response to the user 120. A visual response may be provided using a light pattern of one or more colors and/or sequences. For example, the empathetic computing device 110 may generate a light pattern having a semicircular shape to emulate a smile. In another example, the empathetic computing device 110 may generate a pattern having a circular shape to indicate it is being held. An auditory response may be generated using a speaker or other mechanism of sound generation, and may include various discrete sounds and tones. And auditory response may be provided using a speaker and may include a sound of virtually any frequency, amplitude, or pattern. For example, the empathetic computing device 110 may generate a sound varying in pitch imitating a rising or falling intonation or may generate a sound mimicking one or more particular human generated sounds (e.g., laughter). A vibrational response may be provided using a vibrator motor or a piezo-actuated vibrator and may include any manner of shaking, trembling and vibrating (silently or audibly). For example, the empathetic computing device 110 may generate a relatively long vibration in response to the user 120 approaching the empathetic computing device 110 and may generate a relatively short vibration in response to the user 120 touching the empathetic computing device 110. In another example, the empathetic computing device 110 may generate a vibration such that an orientation of the empathetic computing device is adjusted. The empathetic computing device may, for instance, generate vibrations such that the empathetic computing device 110 rotates clockwise, rotates counterclockwise, rolls, sways, and/or slides. Such movements may be used to generate movement mimicking one or more particular human generated movements (e.g., nodding). In some instances, the empathetic computing device 110 may vibrate such a camera of the empathetic computing device 110 is pointed at the user 120. In this manner, the empathetic computing device 110 may provide a response, at least in part, by "looking" at the user 120 and/or determining an expression of the user 120.

The manner in which the empathetic computing device 110 responds may be determined in accordance with one or more modes. Based on identified events, the empathetic computing device 110 may select a mode, and based on the selected mode, may provide a response to the user 120. By way of example, the empathetic computing device 110 may enter a first mode due to the user 120 touching the empathetic computing device 110 and may enter a second mode due to the user 120 clasping the empathetic computing device 110. In the first mode, the empathetic computing device 110 may provide a first response (e.g., a light pattern) and in the second mode, the empathetic computing device 110 may provide a second response (e.g., a vibration). Because the empathetic computing device 110 may identify events in real-time, the empathetic computing device 110 may change modes and/or provide responses in real-time. In some instances, the empathetic computing device 110 may identify concurrent events associated with the user 120. For example, a user 120 may alternate between laughing and talking while touching the empathetic computing device 110, or conversely, change the manner is which the empathetic computing device 110 is held while talking. Accordingly, the empathetic computing device 110 may select a mode based on concurrently identified events.

In some examples, the empathetic computing device 110 may weight identified events and choose a mode based on the weighted events. The weight of an event may be based on the type of event and/or characteristics of the event. For example, an event directed to a user 120 speaking may be weighted based on the volume, clarity, duration, and/or context of the user 120's speech during the event.

In this manner, an empathetic interface may be achieved between the user 120 and the empathetic computing device 110. By responding with patterns of light, sound, vibration, etc. and reacting to natural movements of the user 120, a humanized connection may be formed between the user 120 and the empathetic computing device 110, which may advantageously make communication between the 120 and the device 110 pleasurable and easy.

Figure 2A:
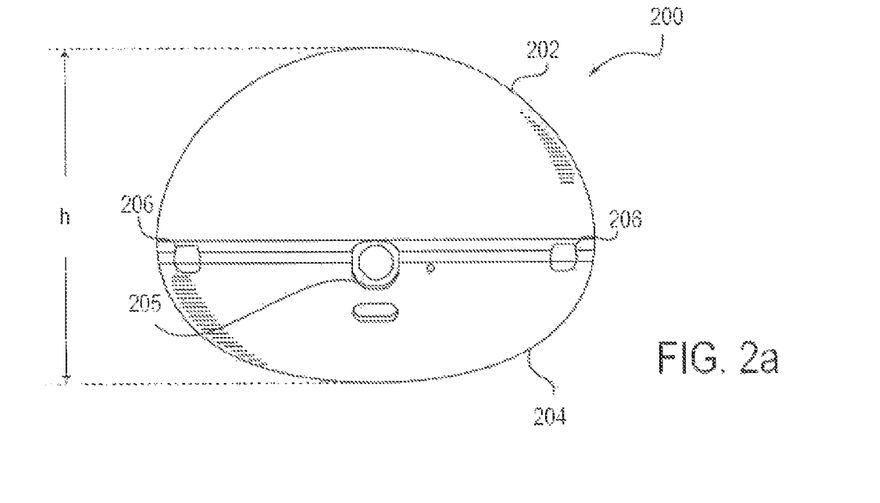
FIG. 2a is a side view of an empathetic computing device according to an embodiment of the present invention.
Figure 2B:
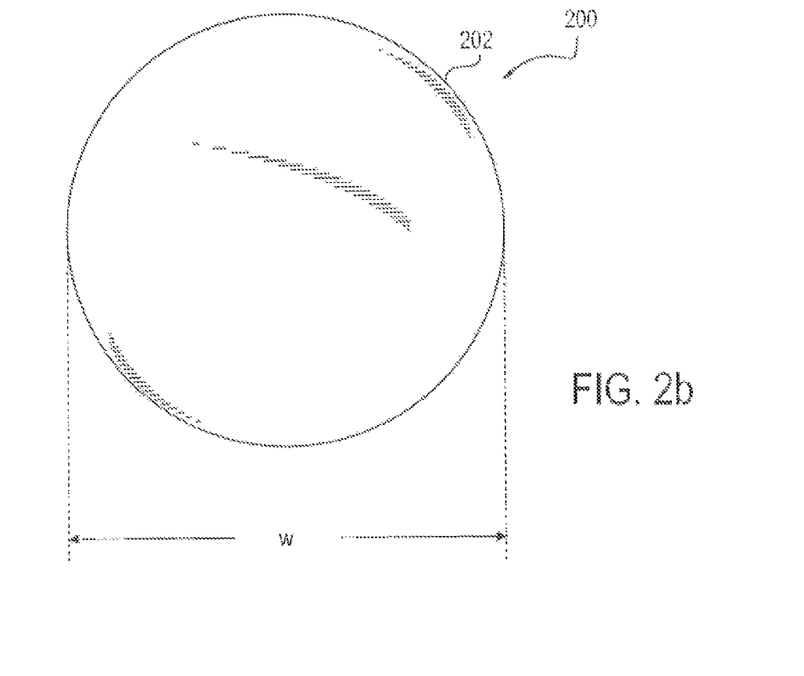
FIG. 2b is a top view of an empathetic computing device according to an embodiment of the present invention.

FIGS. 2a and 2b are a side view and top view of an empathetic computing device 200, respectively, according to an embodiment of the present invention. The empathetic computing device 200 may be used to implement the empathetic computing device 110 of FIG. 1. The empathetic computing device 200 may include an upper portion 202, a lower portion 204, a camera 205, and infrared sensors 206.

Generally, the empathetic computing device 200 may be a portable, handheld device having a relatively spherical shape. The empathetic computing device 200 may be palm-sized such that a user 120 may hold (e.g., grasp) the empathetic computing device using a single hand. For example, a palm-sized device may rest in a palm of a user and be sized to fit within the palm. The size may further be such that, when resting in the palm a user may curl their fingers over substantially the entire device. By way of example, with reference to FIG. 2a, the empathetic computing device may have a height of 43.5 mm, and with reference to FIG. 2b, the empathetic computing device 200 may have a width of 56 mm. In other examples, the empathetic computing device 200 may have other heights and widths. The enclosure of the empathetic computing device may have any color, texture, and/or composition.

The upper portion 202 and lower portion 204 may form the enclosure of the empathetic computing device 200. In some examples, the upper portion 202 and lower portion 204 may latch together to form the enclosure, and may be separated using a button (not shown). The upper portion 202 may be substantially hemispherical in shape, and the lower portion 204 may be substantially hemi-ellipsoidal in shape such that the empathetic computing device 200 may maintain a static position when rested on a relatively level surface. In other examples, the upper portion 202 and lower portion 204 may have different shapes. For example, in some instances, the upper portion 202 and lower portion 204 may be substantially hexahedronal (e.g., rectangular hexahedronal) in shape.

The upper portion 202 may be partially or fully translucent such that light may pass into and/or out of the upper portion 202. In this manner, visual responses may be provided to the user 120 using, for instance, a plurality of LEDs included in the empathetic computing device 200. The lower portion 204 may be substantially opaque. As will be described in further detail, the lower portion 204 may include one or more other components of the empathetic computing device 200, such as one or more sensors used for generated user data.

By having a translucent upper portion 202, a user 120 may be able to distinguish between various light patterns provided by the device 110 and thereby associate particular light patterns with particular responses. By having a partially translucent upper portion 202, a user 120 may be able to see the light patterns produced by the device 110, but may not clearly identify individual light sources or electronic components inside the device 110. In this manner, the user 120 may form a more interpersonal connection with the device in that the electronic components may be obscured, humanizing the device.

In some examples, the upper portion 202 and/or the lower portion 204 may include one or more buttons (not shown) that may be used to facilitate operation of the empathetic computing device 200. For example, in at least one embodiment, the lower portion 204 may include a button for performing various functions, such as turning the empathetic computing device 200 on and off, restarting (e.g., rebooting) the empathetic computing device 200, and/or updating the empathetic computing device 200. Buttons included in this manner may be tactile or may be touch-sensitive.

Figure 2C:
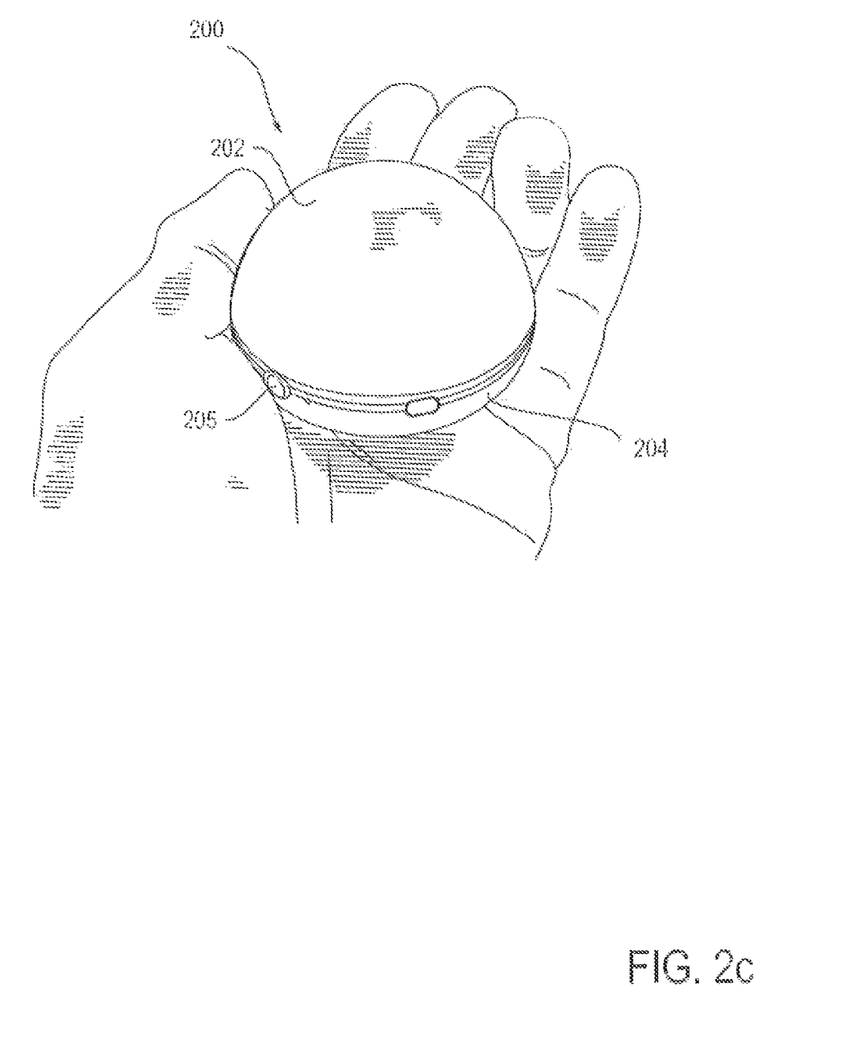
FIG. 2c is a perspective view of an empathetic computing device according to an embodiment of the present invention.

FIG. 2c is a perspective view of the empathetic computing device 200 according to an embodiment of the present invention. As illustrated, the empathetic computing device 200 may be a palm-sized device allowing a user 120 to hold the empathetic computing device 200 using a single hand. While in FIG. 2c the empathetic computing device 200 is shown as being partially grasped, it will be appreciated that the empathetic computing device 200 may alternatively be touched by a user 120, supported by the palm of a user 120, fully grasped using a single hand of a user 150, or clasped using two hands of a user 120 such that the empathetic computing device 200 is substantially enclosed by the two hands. Each of the aforementioned actions may cause the device to provide a particular response, or enter a particular mode.

Figure 3A:
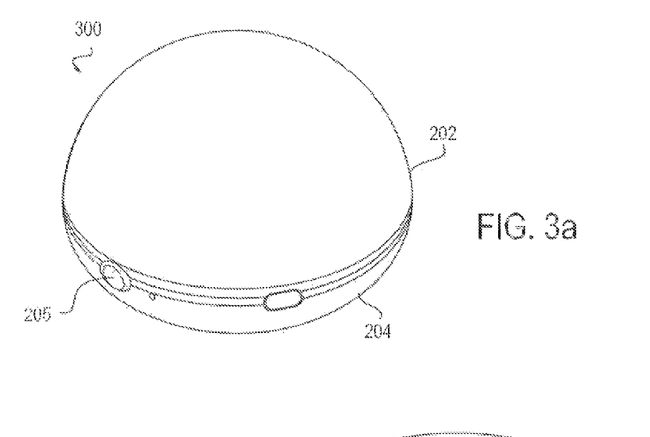
FIG. 3a is a perspective view of an empathetic computing device according to an embodiment of the present invention.

FIG. 3a is a perspective view of an empathetic computing device 300 according to an embodiment of the present invention. The empathetic computing device 300 may be used to implement the empathetic computing device 200 of FIGS. 2a-2c. The empathetic computing device 300 includes elements that have been previously described with respect to the empathetic computing device 200 of FIGS. 2a-2c. Those elements have been shown herein using the same reference numbers used in FIG. 2 and operation of the common elements is as previously described. Consequently, a detailed description of the operation of these elements will not be repeated in the interest of brevity.

Figure 3B:
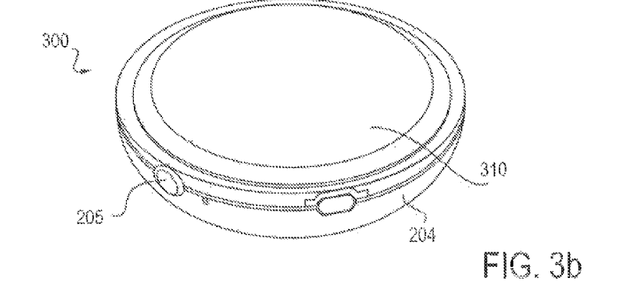
FIG. 3b is a perspective view of an empathetic computing device according to an embodiment of the present invention.

FIG. 3b is a perspective view of the empathetic computing device 300 according to an embodiment of the present invention. Relative to FIG. 3a, the upper portion 202 of the empathetic computing device 300 is not shown. As illustrated, the empathetic computing device 300 includes an optic device 310. The optic device 310 may be a diffuser, beam splitter, and/or one-way mirror and may adjust light provided by one or more components located within the lower portion 204, discussed further herein. The optic device 310 may be any light adjusting device known in the art including ground glass diffusers, Teflon diffusers, holographic diffusers, opal glass diffusers, greyed glass diffusers, prisms, and half-silvered mirrors. By using an optic device 310, light provided by the device 110 may be split, scattered and/or "softened," thereby reducing recognition of individual light sources of the device 110. The optic device 310 may further conceal one or more electronic components inside the device 110 from the user 120, for instance, by reflecting ambient light. In this manner, the optic device 310 may further humanize the device 110.

Figure 3C:
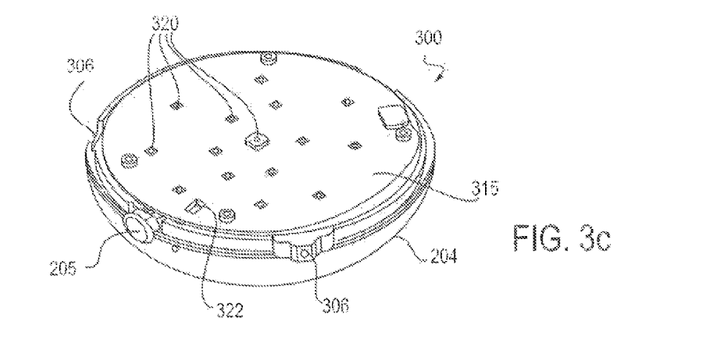
FIG. 3c is a perspective view of an empathetic computing device according to an embodiment of the present invention.

FIG. 3c is a perspective view of an empathetic computing device 300 according to an embodiment of the present invention. Relative to FIG. 3b, the optic device 310 of the empathetic computing device 300 is not shown. As illustrated, the empathetic computing device 300 may include a plurality of infrared sensors 306 and an interface board 315.

Each of the infrared sensors 306 may determine the proximity of the user 120 to the empathetic computing device 300 and may be any infrared sensor known in the art, such as passive infrared sensors. As illustrated, in some examples, infrared sensors 306 may be disposed around a circumference of the empathetic computing device 300. In other examples, the infrared sensors 306 may be located in other locations of the empathetic computing device 300.

The interface board 315 may include a plurality of light emitting devices, such as light emitting diodes (LEDs) 320. Each of the LEDs 320 may provide light through the optic device 310 and the and the upper portion 202 to provide light patterns of visual responses to a user 120. Each of the LEDs 320 may provide light having any intensity and/or color. While shown as being arranged in a particular pattern (e.g., a spiral), the LEDs 320 may be arranged within the interface board 315 in any desired pattern, such as a grid. The interface board 315 will be explained in further detail herein (see FIG. 4).

Figure 3D:
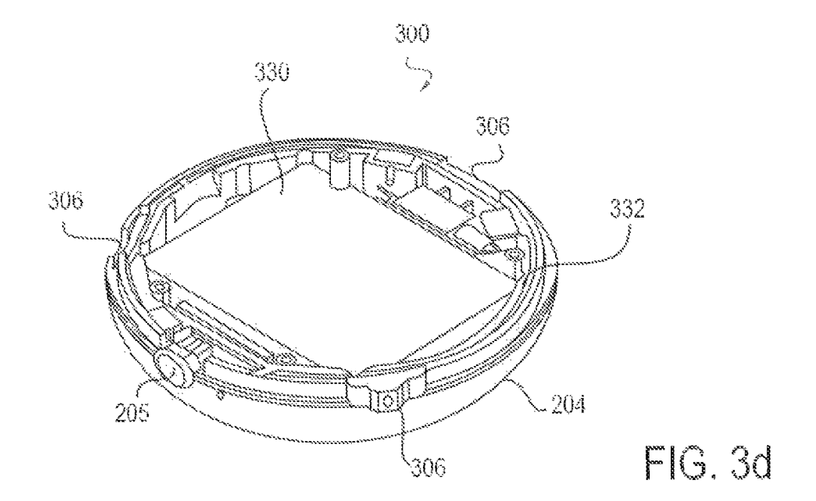
FIG. 3d is a perspective view of an empathetic computing device according to an embodiment of the present invention.

FIG. 3d is a perspective view of an empathetic computing device 300 according to an embodiment of the present invention. Relative to FIG. 3c, the interface board 315 is not shown. As illustrated, the empathetic computing device 300 may include a battery 330 and a touch sensor 332. The battery 330 may be any battery, including for example, rechargeable batteries, known in the art and may store and provide power to various components of the empathetic computing device 300.

The touch sensor 332 may include a touch sensor belt disposed circumferentially about the empathetic computing device 300 and may detect when a user 120 touches any portion of the empathetic computing device 300 where the touch sensor 332 is disposed. The touch sensor 332 may be capacitive, resistive, piezoelectric, or a combination thereof.

Figure 3E:
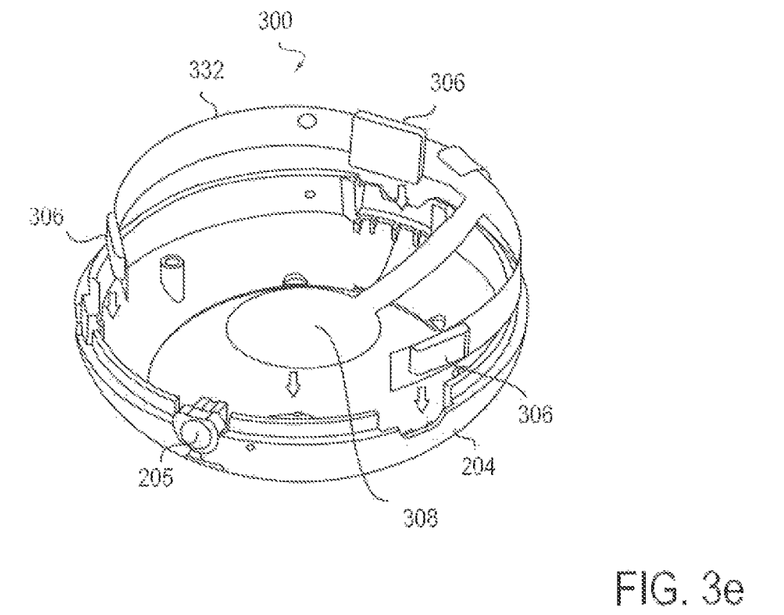
FIG. 3e is an exploded perspective view of an empathetic computing device according to an embodiment of the present invention.

FIG. 3e is an exploded perspective view of an empathetic computing device 300 according to an embodiment of the present invention. Relative to FIG. 3d, the battery 330 is not shown. A illustrated, the touch sensor 332 may include a touch pad 308. The touch pad 308 may include a plurality of radial electrode lines radially extending from the center of the touch pad 308 and may determine whether the empathetic computing device 300 is supported by a surface, such as a table or a palm of the user 150. In some examples, the infrared sensors 306 may be periodically disposed along the touch sensor belt of the touch sensor 332.

Figure 4:
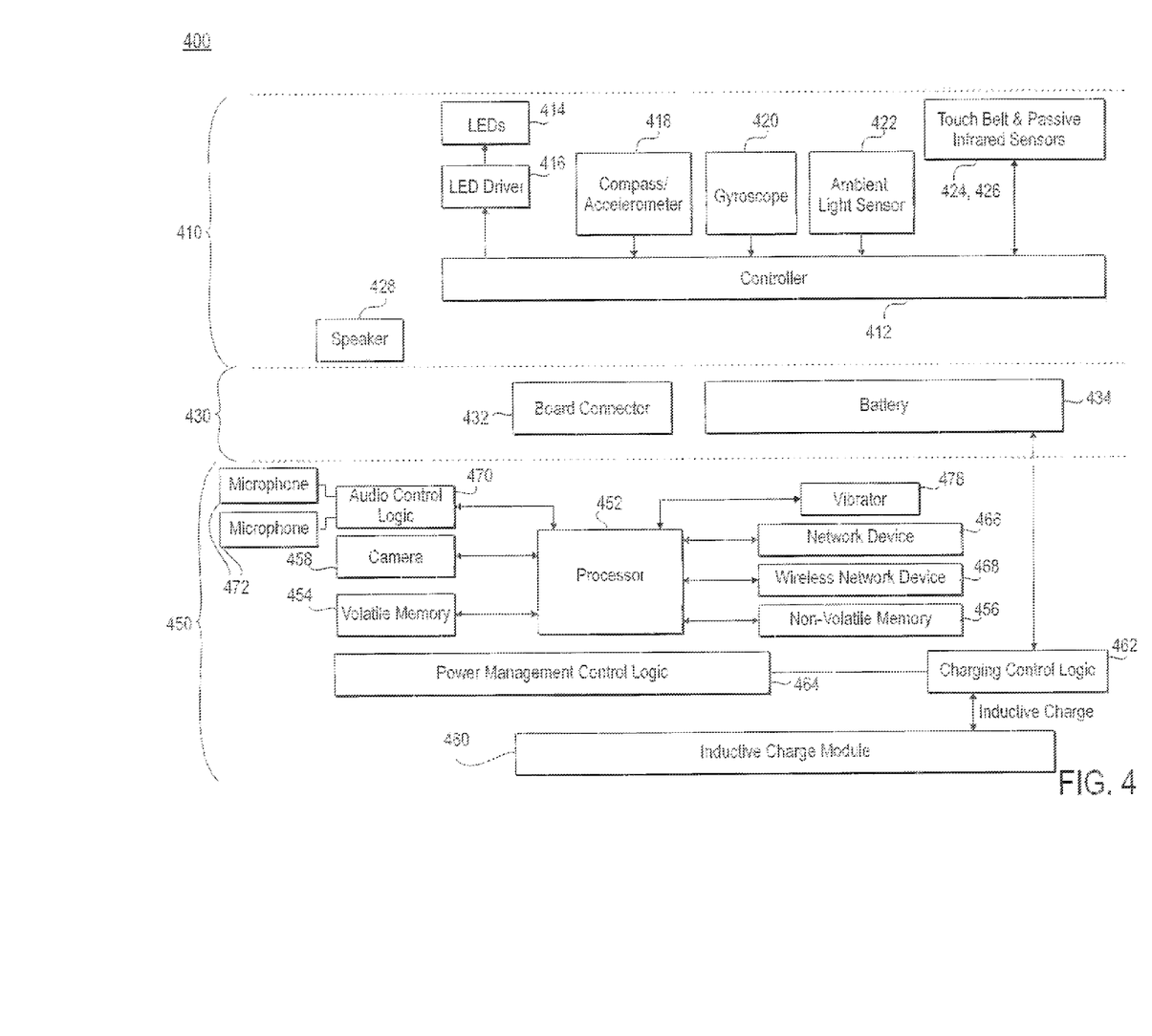
FIG. 4 is a block diagram of an empathetic computing device according to an embodiment of the present invention.

FIG. 4 is a block diagram of an empathetic computing device 400 according to an embodiment of the present invention. The empathetic computing device 400 may be used to implement the empathetic computing device 300 of FIGS. 3a-3e. The empathetic computing device 400 may include an interface board 410, a power region 430, and a control board 450. As described, each of the interface board 410, power region 430, and control board 450 may be located in a lower portion of the empathetic computing device 400.

The interface board 410 may include a controller 412 that may receive user data from one or more sensors of the interface board 410. For example, the controller 412 may be coupled to a compass/accelerometer 418, a gyroscope 420, an ambient light sensor 422, a touch sensor 424, and infrared sensors 426, and receive data therefrom. Each of the sensors may provide respective data to the controller 412. The controller 412 may in turn provide the data to the processor 452 such that the data may be used to identify one or more events associated with the user 120, as described herein. In some examples, the controller 412 may filter and/or otherwise modify data received from the sensors prior to providing the data to the processor 452.

As described, the touch sensor 424 may be used to determine whether the user 120 is touching an empathetic computing device, such as the empathetic computing device 110 of FIG. 1. In some examples, the compass/accelerometer 418 and the gyroscope 420 may be additionally or alternatively be used to determine whether the user 120 is touching the empathetic computing device. The gyroscope 420, for instance, may provide signals indicating that the empathetic computing device 110 has been tilted as a result of the user 120 touching the empathetic computing device 110. In this manner, the empathetic computing device 110 may determine whether the user 120 is touching the empathetic computing device even if the user 120 is not touching a portion of the empathetic computing device where the touch sensor 424 is disposed. In some examples, the frequency at which the empathetic computing device 120 sways back and forth may be used to determine the manner in which the user 120 has touched the empathetic computing device 110. A lower frequency (due to larger sways) may, for instance, indicate a more forceful touch.

The interface board 410 may further include an LED driver 416 and LEDs 414 that may provide visual responses to a user 120. For example, the controller 412 may cause the LED driver 416 to illuminate one or more of the LEDs 414 to provide a specified light pattern of a particular visual response. The interface board 410 may further include a speaker 428 that may provide auditory responses to the user 120. Auditory responses may be based on one or more audio signals received from the audio control logic 470, described in further detail below.

The power region 430 may be located between the interface board 410 and the control board 450 and include a board connector 432 and a battery 434. The board connector 432 may provide data between respective components of the interface board 410 and the control board 450. For example, the board connector 432 may provide signals from the audio control logic 470 to the speaker 428. For the sake of clarity, specific connections provided by the board connector 432 are not shown in FIG. 4. The power region 430 may further include a battery 434. The battery 434 may store and/or provide power to one or more components of the empathetic computing device 400.

The control board 450 may include a processor 452. Generally, the processor 452 may govern operation of the empathetic computing device 400 and may execute one or more computer readable instructions stored in the non-volatile memory 456 such that the empathetic computing device may operate as described herein.

The processor 452 may receive data from one or more of the devices of the control board 450. For example, the processor 452 may receive data from the camera 458, network device 466, wireless network device 468, and/or audio control logic 470. The camera 458 may provide visual data associated with the user 120, such as a facial expression or natural action of the user 120. The network device 466 may communicate with one or more wired networks, such as a USB network or Ethernet network, and the wireless network device 468 may communicate with one or more wireless networks. Accordingly, the network device 466 and/or the wireless network device 468 may allow the processor 425 to communicate with one or more external devices using a wired or wireless network. In some examples, the network device 466 and/or wireless network device 468 may be used to determine a location of the empathetic computing device 400. The audio control logic 470 may be coupled to one or more microphones 472 and may receive audio data (e.g., voice data) associated with the user 120. The audio control logic 470 may provide audio data to and receive audio data from the processor 452. Audio data may be provided from the microphones 472 to the processor 452, and may be provided from the processor 452 to the speaker 428. In some examples, the audio control logic 470 may include one or more analog-to-digital converters and digital-to-analog converters and/or may further include one or more audio filters or codecs.

The control board 450 may further include a vibrator 478 that may provide vibration responses to a user 120. For example, the processor 452 may cause the vibrator 478 to vibrate in a particular manner during a vibrational response.

The control board 450 may include power circuitry comprising an inductive charge module 460, charging control logic 462, and power management control logic 464. During a charge sequence, the inductive charge module 460 may be coupled to an external device, such as a charging mat or port (not shown) and receive charge from the charging mat. The inductive charge module 460 may provide the charge to the charging control logic 462. In turn, the charging control logic 462 may charge the battery 434. When either the battery 434 is fully charged, or the inductive charge module 460 is no longer coupled to the external device, the charging control logic 462 may end the charging sequence. The power management control logic 464 may manage allocation of power to components of the empathetic computing device 400. In some examples, the empathetic computing device may include a coil (not shown) for inductive charging. The coil may be stacked with (e.g., over or under) a touch pad, such as the touch pad 308 of FIG. 3. During a charging sequence, the coil may experience eddy current and because the touch pad 308 is stacked with the coil, the touch pad 308 may experience eddy current as well. Because, as described, the touch pad 308 may include a plurality of radial electrode lines, the touch pad 308 may minimize induction heating resulting from eddy current. For example, each of the radial electrode lines of the touch 308 may be perpendicular to an adjacent portion of the coil and in this regard minimize the inducement of eddy current and the induction heating resulting therefrom. In at least one example, the touch pad 308 may be substantially circular in shape and/or may include one or more perforations such that the touch pad is substantially similar to a trefoil, quatrefoil, cinquefoil, and/or clover in shape.

In some examples, the empathetic computing device 400 may selectively enable one or more components according to a mode of the empathetic computing device 400. In this manner, the empathetic computing device 400 may increase power usage efficiency. By way of example, the empathetic computing device 400 may determine that a user 120 is not proximate and enter a corresponding mode. In response, the processor 452 may enter low power operation (e.g., sleep mode). In at least one embodiment, the power management control logic 464 may cause the processor 452 to enter low power operation, for instance, responsive to the user 120 not being proximate to the empathetic computing device 400 for a particular amount of time. While the processor 452 is in low power operation, the controller 412 and one or more sensors of the empathetic computing device, such as the infrared sensors 426 or microphones 472, may continue to operate. Responsive to the one or more sensors detecting that a user 120 is proximate the empathetic computing device 400, the processor 452 may exit the low power operation and begin processing user data.

In some examples, other features and/or components of the empathetic computing device 400 may be selectively enabled as well. Speech analysis, for example, may be selectively enabled (e.g., by the processor 452) based on whether the empathetic computing device 400 is in a user 120's hand. In another example, the camera 458 may be selectively enabled based on whether the user 120 is proximate the empathetic computing device 400 and/or whether the empathetic computing device 400 is near the user 120's face.

In some examples, the empathetic computing device 400 may select a mode based on whether the empathetic computing device 400 is charging. In response, the empathetic computing device 400 may selectively enable one or more features and/or components of the empathetic computing device 100. For example, the empathetic computing device 400 may remain connected to one or more available wireless networks when charging. Additionally or alternatively, the empathetic computing device 400 may transfer and/or backup data to a computing device, such as the computing device 130 of FIG. 1, when charging.

In some examples, the interface board 410 and control board 450 may each be an integrated circuit, and accordingly, respective components of the interface board 410 and control board 450 may be integrated. In other examples, one or more respective components may not be integrated in either of the interface board 410 and the control board 450. Moreover, while particular components have been described as being located in the interface board 410, power region 430, or control board 450, it will be appreciated that in other embodiments components of the empathetic computing device 400 may be arranged in other configurations. The compass/accelerometer 418 and/or the gyroscope 420, for instance, may be included in the control board 450 and/or the audio control logic 470 may be located in the interface board 410.

As described, the device 110 may enter and/or transition between one or more modes during operation based on one or more indentified events. Thus, in many instances, the device 110 may enter a mode based on the interaction of the user 120 with the device 110. Example modes may include a play mode, a wish mode, a feel mode, a like mode, a smile mode, and/or one or more proximity modes. The device 110 may enter the play mode when resting on the palm of a user 120. The device 110 may enter the wish mode when a user 120 is speaking and the device 110 is supported on a palm near the face of the user 120. The device 110 may enter the feel mode when the user 120 fully grasps the device 110. The device 110 may enter the like mode when supported on a flat surface (e.g., table) and touched by the user 120. The device 110 may enter the smile mode when a user 120 is laughing and the device 110 is supported on a flat surface. Proximity modes may include various modes based on proximity of the user 120 to the device 110. By way of example, the device 110 may enter a first proximity mode when near a user 120, may enter a second proximity mode when partially grasped by a user 120, and may enter a third proximity mode when clasped by a user. It will be appreciated that the foregoing examples of modes are provided as example only and that other implementations may be used.

Figure 5:
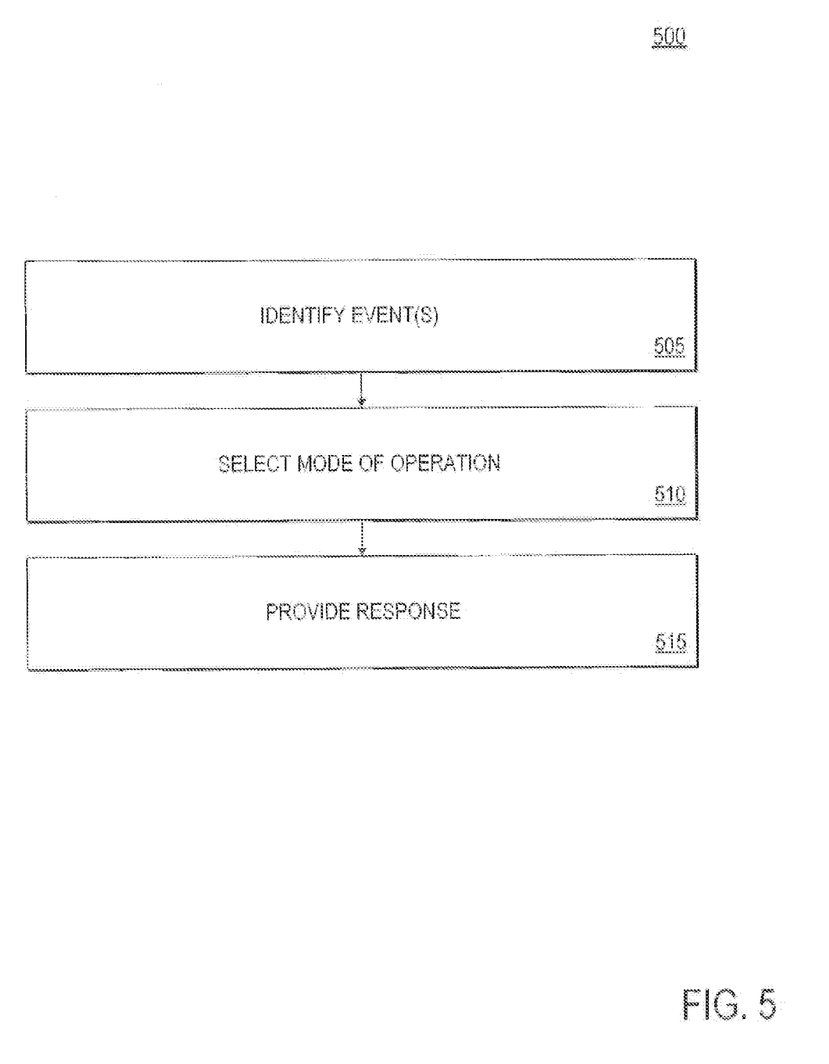
FIG. 5 is a flowchart of a method for interfacing with a user according to an embodiment of the present invention.

FIG. 5 is a flowchart of a method 500 for interfacing with a user according to an embodiment of the present invention. The method 500 may be performed by empathetic computing devices described herein, such as the empathetic computing device 110 of FIG. 1. At step 505, the device 110 may identify one or more events associated with the user 120. As described, identifying events may include identifying natural actions of the user 120 and/or user interaction with the empathetic computing device 110. Natural actions may include laughing, talking, winking, making a facial expression (e.g., smiling, frowning), or a combination thereof, and user interaction may include proximity of the user 120 and differentiate whether the user 120 is touching, supporting (e.g., on a flat or curved palm), partially grasping, fully grasping, and/or clasping the device 110. Events may be identified based on user data generated by the device 110.

In some examples, events may include any of the following natural actions and/or user interaction. Events may include the user 120 approaching and/or remaining near the device 110 for a particular period of time; moving away from the device 110, speaking with another human and/or the device 110; laughing; using particular tones of voice; lifting, carrying, spinning, touching, shaking, supporting, vertically pinching, horizontally pinching, covering, clasping, dropping, catching, grasping, ungrasping, pushing, holding, and/or walking with the device 110; removing and/or returning the device 110 from a charging mat; leaving and/or returning home with the device 110; placing the device 110 in a dark environment (e.g., purse or pocket); looking at the device; bringing the device 110 close to the user 120's face and/or torso; and/or holding the device 110 away from the user 120's body, for instance, by extending the elbow. Events may further include increases or decreases in ambient brightness.

Once one or more events have been identified, at step 510, the device 110 may select (and enter) a mode of operation based on the identified events. By way of example, the device 110 may enter the feel mode responsive to the user 120 grasping the device 110. As described, modes may include a play mode, a wish mode, a feel mode, a like mode, a smile mode, and one or more proximity modes. It will be appreciated that other modes may be available as well and those described are provided as examples.

At step 515, the empathetic computing device 110 may provide a response to the user 120 based on the selected mode. As described, responses may be visual, auditory, and/or vibrational. For example, after entering the feel mode, the device 110 may provide a particular light pattern to the user 120 associated with the feel mode.

Figure 6:
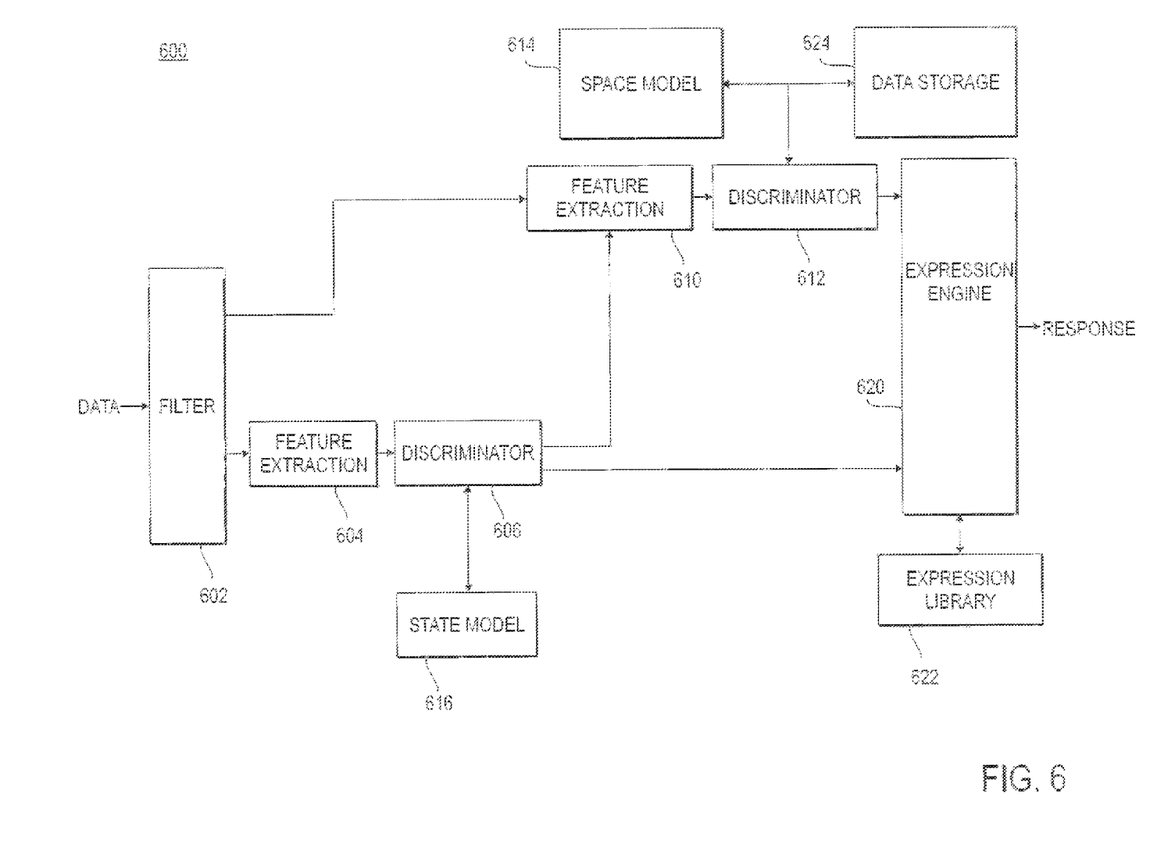
FIG. 6 is a schematic block diagram of a process flow that may be performed by an empathetic computing according to an embodiment of the present invention.

FIG. 6 is a schematic block diagram of a process flow 600 that may be performed by an empathetic computing device according to an embodiment of the present invention. The process flow 600 may include a plurality of functional blocks that may each be performed by an empathetic computing device, such as the empathetic computing device 110 of FIG. 1.

A filter 602 may receive user data provided from one or more sensors of the empathetic computing device and filter the user data, for instance, during a pre-process operation. The filter may include signal processing filters including, but not limited to, low pass filters, high pass filters, band pass filters, moving average filters, zero crossing filters, transform filters (e.g., FFT filters), class label filters, class label timeout filters or a combination thereof. In some examples, the filter 602 may provide filtered user data in real time.

Once filtered, user data may be provided to a feature extraction block 604 and a discriminator block 606 for selection of an initial mode. For example, the feature extraction block 604 may receive the user data and perform feature extraction on the user data. Performing feature extraction may convert the user data to feature data by selectively removing portions of the user data. In performing feature extraction, the feature extraction block 604 may discard outlier and redundant user data, normalize the user data, and/or perform one or more other feature extraction tasks. In accordance with know feature extraction methodologies, such as nonlinear dimensionality reduction, the feature data may be provided in vector form. Feature data may include data relating to a user 120 holding, grasping, touching, clasping, or otherwise interacting with the device 110. Feature data may further include data relating to one or more natural movements of the user 120, including but not limited to, waiving, making a facial expression, walking, sitting, standing, and further may include data relating to one or more aspects of a user 120's environment.

The discriminator block 606 may receive the feature data from the feature extraction block 604 and compare the feature data to one or more events models of the model 616. Feature data and event models may include comparing vectors. By comparing the feature data in this manner, an event may be identified. The discriminator block 606 may determine, for instance, that the user 120 is speaking. The empathetic computing device 110 may select and enter an initial mode based on the identified event. As described, example modes may include a play mode, a wish mode, a feel mode, a like mode, a smile mode, and/or one or more proximity modes.

The expression engine 620 may receive the initial mode from the discriminator block 606 and provide a response based on the initial mode. In some examples, the expression engine 620 may compare the initial mode to expression models of the expression library 622. Based on the comparison, the expression engine 620 may select a response and provide the same. As described, the response may be visual, auditory, and/or vibrational.

The user data may also be provided to a feature extraction block 610 and a discriminator block 612 for selection of a weighted mode. For example, once an event has been identified, a feature extraction block 610 may receive user data associated with the identified event for the duration of the event and further may receive the initial mode selected by the discriminator block 606. The feature extraction block 610 may continuously perform feature extraction on the user data as it is received during the event. The feature extraction block 610 may perform feature extraction in substantially the same manner as the feature extraction block 604.

The discriminator block 612 may receive feature data from the feature extraction block 610, and based on the feature data, may select a weighted mode. For example, the identified event may be weighted based on the feature data. The weighted event may be compared to data models of a model 614 (e.g., space model), and based on the weighting of the identified event, the empathetic computing device 110 may select (and enter) a weighted mode that may be different from the initial mode. In some examples, the selected mode may be based on the initial mode. For example, one or more weighted modes may be selected only when the empathetic computing device 110 has a particular initial mode.

An event may be weighted according to the "closeness" of the empathetic computing device to the user 120 during the event as indicated by feature data associated with the event. This may include the proximity of the user 120, the user 120's face, and/or the user 120's body during the event, interaction of the user 120 with the empathetic computing device 110 and the duration thereof, the orientation of the empathetic computing device 110, and stability of the empathetic computing device 110. For example, the user 120 grasping the empathetic computing device 110 may be weighted a first amount when the user 120 grasps for a relatively brief amount of time and may be weighted a second amount when the user 120 grasps for a relatively long amount of time. An event may further be weighted according to the "context" of the user 120 as indicated by feature data associated with the event. This may include determining the clarity, complexity, duration, and articulation of the user 120's speech, as well as the amount of ambient noise and light of the user 120's environment. The volume of ambient noise, for example, may impact the weighting of an event. An event may further be weighted according to "continuity," "constancy," and/or "consistency" of actions of the user 120. Because a user 120's actions may be tracked over a period of time, this may include weighting according to the frequency, duration, and/or reception of those actions.

The expression engine 620 may receive the weighted mode from the discriminator block 612 and provide a response based on the weighted mode. In some examples, the expression engine 620 may compare the weighted mode to expression models of the expression library 622 and provide a response based on the comparison. As described, expressions provided by the device 110 may be visual, auditory, and/or vibrational. For example, expressions may include various light patterns emulating shapes such as spirals, circles, semicircular curves, helices, rectangular shapes, stars, and using one or more colors.

Because over the duration of the event, feature data associated with the event may be continuously received, the weighting of the identified event may be continuously adjusted as well. Accordingly, multiple weighted modes may be selected over the duration of an event as the weighting is continuously adjusted. In some examples, the expression engine 620 may provide a respective response in accordance with each selected mode such that the empathetic computing device may provide several responses for a particular event.

At the conclusion of an event, one or more aspects of the event may be captured. For example, each of the selected modes, as well as any responses provided by the user 120 may be stored in the data storage 624. In some instances, the expression engine 620 may provide a response indicating that the event has been captured. Data associated with an event may be stored in vector form.

Other data may be stored as well. The empathetic computing device 110 may capture video, audio, or other data associated with particular events. This data may be subsequently accessed by a user 120 using the empathy interface or using another device, such as the computing device 130. As an example, a user 120 may grasp the device 110 and in response the device 110 may enter a mode in which a period of audio may be buffered and/or stored in the device 110. In some examples, audio may be continuously buffered such that audio buffered prior to entering a mode may be stored responsive to entering the mode. In other examples, audio may only be buffered in response to entering a particular mode.

Over time, data may be accumulated in the data storage 624 and may be used to select a weighted mode. For example, correlations derived from data stored in data storage 624 may be used to predict events, and the empathetic computing device 110 may enter mode associated with predicted events. Stored data may further be used to adjust weighting parameters. If a type of event is relatively common, weighting applied to he type of event may be increased or may be decreased. For example, if a user 120 talks to the device 110 at a same time on a regular basis, the device 110 may predict that a user 120 will speak to device 110 at the time and enter a mode accordingly. The device 110 may, for instance, provide a light expression to the user 120 notifying the user 120 that the time at which the user 120 typically speaks to the device 110 is near.

While the process flow 600 is described with the respect to a single event, it will be appreciated by those having ordinary skill in the art that multiple events may be identified in parallel and/or in combination. In this manner, modes of the empathetic computing device may be determined based on multiple concurrent and/or sequential events.

Each of the functional blocks of the process flow 600 may be implemented in software and/or hardware of the empathetic computing device 110. For example, in at least one embodiment, the filter 602 may be implemented in hardware and the remaining functionally blocks may be implemented in software and executed by the processor 452. In other examples, all of the functional blocks may be implemented in software and stored, for instance, in a non-volatile memory of the empathetic computing device 110.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An empathetic computing device, comprising:
   an enclosure configured to fit into a palm of a user and having an upper portion and a lower portion, the enclosure comprising:
   an interface board having a plurality of light emitting devices configured to provide a light pattern of a visual response;
   a processor coupled to a memory device; and
   a touch sensor configured to detect a touch of the user, comprising:
   a touch belt disposed along the enclosure circumferentially; and
   a touch pad.

2. The empathetic computing device of claim 1, wherein the upper portion of the enclosure is partially translucent.

3. The empathetic computing device of claim 1, wherein the enclosure further comprises a plurality of infrared sensors configured to determine proximity of the user to the empathetic computing device.

4. The empathetic computing device of claim 1, wherein the upper portion is substantially hemispherical.

5. The empathetic computing device of claim 1, wherein the interface board further comprises an ambient light sensor.

6. The empathetic computing device of claim 1, wherein the light emitting devices comprise light emitting diodes.

7. The empathetic computing device of claim 1, further comprising:
   an optic device configured to adjust light of the light pattern.

8. The empathetic computing device of claim 1, wherein the touch pad comprises a plurality of radial electrode lines.

9. An empathetic computing system, comprising:
   a palm-sized empathetic computing device including a plurality of sensors, a processor, and a memory coupled to the processor, the palm-sized empathetic computing device configured to enter a mode responsive to identification of an event and provide a visual response indicative of the mode,
   wherein the event is based on a proximity of a user to the palm-sized empathetic computing device, a natural action of the user, interaction of the user with the palm-sized empathetic computing device, or a combination thereof.

10. The empathetic computing system of claim 9, wherein the visual expression comprises a light expression.

11. The empathetic computing system of claim 9, wherein the user interaction comprises touching, supporting, partially grasping, fully grasping, clasping, or a combination thereof.

12. The empathetic computing system of claim 9, wherein the palm-sized empathetic computing device is further configured to store data associated with the event responsive to the event concluding.

13. The empathetic computing system of claim 9, wherein the mode is an initial mode and wherein the palm-sized empathetic computing device is further configured to weight the event to provide a weighted event and enter a weighted mode based on the weighted event and the initial mode.

14. The empathetic comparing system oh claim 9, wherein the palm-sized empathetic computing device is further configured to selectively enable one or more features, one or more components, or a combination thereof, based on the event.

15. A method of interfacing with a user, comprising:
   receiving a first set of user data;
   identifying an event based on the first set of user data;
   selecting an initial mode based on the event;
   providing, using a light device, a first response to the user based on the initial mode;
   receiving a second set of user data;
   weighting the event based on the second set of user data to provide a weighted event;
   selecting a weighted mode based on the weighted event and the initial mode; and
   providing, using the light device, a second response to the user based on the weighted event.

16. The method of claim 15, further comprising:
   filtering the user data.

17. The method of claim 15, wherein identifying an event based on the user data comprises performing feature extraction on the user data.

18. The method of claim 15, wherein providing, using a light device, a first response to the user based on the initial mode comprises providing an auditory response.

19. The method of claim 15 wherein providing, using a light device, a first response to the user based on the initial mode comprises providing a vibrational response.

20. The method of claim 15, wherein the weighted event is a first weighted event, the method further comprising:
   weighting the event based on the user data to provide a second weighted event; and
   providing a third response to the user based on the second weighted event.

21. The method of claim 15, further comprising:
   storing data associated with the event.

22. The method of claim 15, wherein identifying an event based on the user data comprises comparing the user data to a data model.

23. The method of claim 15, wherein weighting the event based on the user data to provide a weighted event comprises weighting the event based on a duration of the event.

* * * * *